United States Patent [19]

Buller

[11] Patent Number: 4,908,310
[45] Date of Patent: Mar. 13, 1990

[54] WATER INSOLUBLE POLYSACCHARIDE POLYMER AND METHOD THEREOF

[75] Inventor: Clarence S. Buller, Lawrence, Kans.

[73] Assignee: University of Kansas, Lawrence, Kans.

[21] Appl. No.: 137,367

[22] Filed: Dec. 23, 1987

[51] Int. Cl.$^4$ ............... C12P 19/04; C12P 19/14; C12R 1/07; C07G 17/001

[52] U.S. Cl. ............... 435/101; 435/99; 435/822; 536/1.1; 536/114

[58] Field of Search ............... 435/101, 99, 822; 536/1.1, 114

[56] References Cited

U.S. PATENT DOCUMENTS

| | | | |
|---|---|---|---|
| 3,301,848 | 1/1967 | Halleck | 435/101 |
| 3,822,250 | 7/1974 | Kimura et al. | 435/829 |
| 4,075,405 | 2/1978 | Takahashi et al. | 536/114 |
| 4,202,966 | 5/1980 | Misaki et al. | 536/1.1 |
| 4,329,448 | 5/1982 | Cox et al. | 536/114 |
| 4,355,106 | 10/1982 | Lawford | 435/829 |
| 4,605,736 | 8/1986 | Morgan | 536/114 |
| 4,707,471 | 11/1987 | Larm et al. | 536/1.1 |
| 4,769,363 | 9/1988 | Misaki et al. | 536/1.1 |
| 4,774,093 | 9/1988 | Provonchee et al. | 536/1.1 |

OTHER PUBLICATIONS

*Chemical Abstracts*, Feb. 13, 1984, vol. 100(7), p. 308, #48271(z).
*Chemical Abstracts*, May 12, 1980, vol. 92(19), p. 284, #160231(d).
*Bergey's Manual of Systematic Bacteriology*, vol. 2, pp. 1325–1329, Williams and Wikins Co., Baltimore, Md.
Quality Research Products; 5. Chromatography; 5-2 Column Chromatography.
"Demonstration of Curdlan-Type Polysaccharide and Some Other β-1,3-Glucan in Microorganisms with Aniline Blue" J. Gen. Appl. Microbiol., 22, 1–11, 1976; authors: Itaru Nakanishi; Kazutsugu Kimura; Takshi Suzuki; Michio Ishikawa; Isao Banno; Takeshi Sakane; Tokuya Harada, pp. 1–11.
"Complex Formation of Gel-Forming Bacterial (1→3-β-D-Glucans (Curdlan-Type Polysaccharides) With Dyes in Aqueous Solution" authors: Itaru Nakanisul; Kazuisugu Kimura; Sadao Kursul; Enchiro Yamazaki, #32 (1974), 47–52.
"Curdlan: A Gel-Forming β-1,3-Glucan"; T. Harada; Polysaccharides in Food, 1979; J. M. Blanshard and J. R. Mitchell; Butterworths; #18; pp. 283–300.
"Production of a Firm, Resilient Gel-Forming Polysaccharide by a Mutant of Alcaligenes Faccalis var. Myxogene 10C3" authors: Tokuya Harada; Matsue Masada; Ken Fujimori; Iwao Maeda; Agr. Biol. Chem., vol. 30, No. 2, pp. 196–198, 1966.
"Curdlan: A Bacterial Gel-Forming β-1,3-Glucan"; authors: Tokuya Harada, Akira Misaki; Hiroshi Saito; Archives of Biochemistry and Biophysics, 124, 202–208 (1968).
"Change in Ability of Agrobacterium to Produce Water-Soluble and Water-Insoluble β-Glucans"; authors: M. Hisamatsu, I. Ott; A. Amerura; T. Harada; Journal of General Microbiology (1977), 103, 375–379.
"Properties of Gels Formed by Heat Treatment of Curdlan, a Bacterial β-1,3 Glucan"; authors: Iwao Maeda; Hiroshi Saito, Matsue Masada; Akira Misaki and Tokuya Harada (Agr. Biol. Chem., vol. 31, No. 10, pp. 1184–1188, 1967).
"Properties of Curdlan Gel" authors: Akira Konno, Yasuhiro Azechi and Hiroshi Kimura (Agric. Biol. Chem. 43(1), 101–104, 1979).
"Affinity Chromatography of Klebsiella Arylslsulfatase on Tyrosyl-Hexamethylenediamino-β-1,3-Glucan and Immunoadsorbent" authors: Yoshikatsu Murooka; Moo-Hyun Yim; Takashi Yamada; Tokuya Harada, Biochimica et Biophysics Acta, 485 (1977), 134–14C; pp. 134–140.
"Polysaccharide 13140: A New Thermo-Gelable Polysaccharide" authors: Hiroshi Kimura; Shintaro Moritaka; Masaru, Journal of Food Science, vol. 38 (1973); pp. 668–670.
"Fine Structure of (1→3)-β-D-Glucans: Curdlan and Paramylon" authors: Robert H. Marchessault and Yves Deslandes, Carbohydrate Research, 75 (1979), 231–242.
"The Gelling Mechanism and Relationship to Molecular Structure of Microbial Polysaccharide Curdlan"; authors: W. S. Fulton and E. D. T. Atkins, American Chemical Society, 1980, 0-8412-0589-2/80/47-14-1-385$06.50/0; No. 25, pp. 385–410.
"A $^{13}$C Nuclear Magnetic Resonance Study of Gel--Forming (1→3)-β-D-Glucans, Evidence of the Presence of Single-Helical Conformation in a Resilient Gel of a Curdlan-Type Polysaccharide 13140 from Alcaligenes faecalis var. myxogenes IFO 13140+"; authors: Hazime Saito; Toyokazu Ohki; Takuma Sasaki; Biochemistry, vol. 16, No. 5, 1977; pp. 908–914.
"Electron Microscopic Study on the Ultrastructure of Curdlan Gel: Assembly and Dissociation of Fabrils of Heating"; authors: Tokuya Harada; Atsuo Koreeda; Shigehiko Sato; Nobutami Kasal, J. Electron Microsc., vol. 28, No. 3, 147–153, 1979 (for this article, pp. 149–153).
"Dependence on Chain Length of Antitumor Activity of (1→3)-β-D-Glucan from Alcaligenes Faecalis Var. Myxogenes, IFO 13140, and its Acid-Degraded Products"; authors: Takuma Sasaki; Noriko Abiko; Yukio Sugino; Kazuo Nitta, Cancer Research, No. 38, Feb. 1978, pp. 379–383.
"Antitumor Activity of Carboxymethylglucans Obtained by Carboxymethylation of (1→3)-β-D-Glucan From Alcaligenes Faecalis Var. Myxogenes IFO 13140"; authors: Takuma Sasakl; Noriko Abiko; Kazuo Nitta; Nobuo Takasuka; Yukio Sugino, Europ. J. Cancer., vol. 15, pp. 211–215.

*Primary Examiner*—Johnnie R. Brown
*Assistant Examiner*—Pamela S. Webber
*Attorney, Agent, or Firm*—Hovey, Williams, Timmons & Collins

[57] ABSTRACT

Polysaccharide polymer produced by cultivating bacteria of the genus Cellulomonas such as ATCC 21399 (Cellulomonas sp.), ATCC #482 (*Cellulomonas flavigena*) and ATCC #53703 (*Cellulomonas flavigena* 819) in a suitable medium.

6 Claims, No Drawings

WATER INSOLUBLE POLYSACCHARIDE POLYMER AND METHOD THEREOF

BACKGROUND OF THE INVENTION

This invention relates generally to novel polysaccharide polymers and methods for the production thereof. More particularly, it relates to a class of new polysaccharide polymers which are produced microbiologically from the action of certain bacteria on carbohydrate substrates.

It is known that polysaccharides are produced by the action of certain microorganisms on certain carbohydrates. Thus see Halleck et al 3,301,848 issued Jan. 31, 1967 "Polysaccharides And Methods For Production Thereof". It has now been discovered that certain bacteria of the genus Cellulomonas will produce a very novel and potentially highly useful polysaccharide polymer when incubated in a medium containing carbohydrate source materials. In general, this new class of polysaccharide polymers is characterized by a multiplicity of D-glucose units attached together in a straight chain through B-1,3 linkages.

All of the known Cellulomonas species (those available from deposit) will produce this polymer to a greater or lesser degree under like conditions.

One of the important advantages of the invention resides in the ability of the organisms listed above to produce the said polysaccharide polymer from a plurality of carbohydrate sources. For example, *Cellulomonas flavigena* 819 will produce a polysaccharide polymer from certain selected carbohydrate source materials selected from the group consisting of at least glycerol, glucose, galactose, fructose, sucrose, lactose, starch, and molasses.

A gelable B-1,3 glucan type polysaccharide is made by the aerobic cultivation of certain microorganisms. In some ways, this polymer generally resembles a known (thermally) gelable B-1,3, glucan known as "curdlan", but differs therefrom in certain other ways.

This invention relates to a new gelable polysaccharide polymer designated as *Cellulomonas flavigena* PS 819" or "PS 819" or "Cf/PS 819". More particularly, the invention is concerned with a microbial production of the polymer Cf/PS 819, with the polymer Cf/PS 819 as a new composition of matter exhibiting specific characteristics as well as having many potential applications.

It has been known that a thermally gelable B-1, 3 glucan named "curdlan" is produced by cultivation of a microbial mutant (strain K) of *Alcaligenes faecalis*var. *myxogenes* 10C 3 (see *Agricultural Biological Chemistry*, volume 30, pages 196 et seq, 1966, by Harada et al). Additionally, see Kimura U.S. Pat. No. 3,822,250, issued Jul. 2, 1974 "Thermo-Gelable Polysaccharide" wherein the inventors found that a mutant (strain NTK-u) of the said strain K can also produce a thermally gelable B-1, 3 glucan type polysaccharide giving a new thermo-gelable polysaccharide designated as "PS". It was also shown that other microorganisms such as *Agrobacterium radiobacter* can also produce such new PS polysaccharide with substantially the same physicochemical properties.

A principal object of the present invention is, therefor, to provide the newly found, gelable polysaccharide polymer Cf/PS 819.

Another object of this invention is to provide methods for producing polymer Cf/PS 819 by means of cultivation of a microorganism and subsequent purification of the product thereof.

Another object of the invention is to provide a new and useful polysaccharide polymer, as well as the process for its production, such polymer being synthesized by certain gram-positive, rod shaped bacteria (genus Cellulomonas) when they are cultured aerobically in a minimal salts medium containing a variety of carbohydrates and/or polysaccharides as carbon and energy sources.

Yet another object of the invention is to provide such a new glucan-type polysaccharide polymer that is synthesized by such microorganism and typically deposited externally thereof as a capsule about the bacteria.

The present invention relates to the production of a new and useful polysaccharide polymer by the treatment of the glucan type polysaccharide polymer that is synthesized and deposited (either externally as a capsule about the bacteria or internally as a granule within the bacteria) by a microorganism of the type Cellulomonas when cultured aerobically in a minimal salts medium containing a variety of carbohydrates and/or polysaccharides as carbon and energy sources, by treating the said cultured, extracted cells with specific solubilizing agents and subsequently removing said solubilizing agents by neutralization or water addition to affect gelation.

The present invention is based on the following observations:

(1) That microorganisms isolated from decaying leaf litter have an ability for producing a polysaccharide polymer able to form a gel;

(2) That said microorganisms belong to the genus Cellulomonas;

(3) That the polysaccharide polymer is synthesized and deposited externally as a capsule about the bacteria (or as a granule in the interior of the bacteria);

(4) That such polymer is synthesized by certain gram-positive, rod shaped bacteria (genus Cellulomonas) when such are cultured aerobically in a minimal salts medium containing a variety of carbohydrates and/or polysaccharides as carbon and energy sources;

(5) That said polymer may be extracted from the said Cellulomonas bacteria cells;

(6) That the recovered polysaccharide polymer has the property of forming a gel under defined conditions, as well as being repeatably solubilized and gelled.

Thus, according to the present invention, a polysaccharide polymer characterized by gel formation can be produced by cultivating a polysaccharide-polymer-having-gel-forming property-producing-microorganism belonging to the genus Cellulomonas in a medium containing assimilable carbon sources and nitrogen sources until said polysaccharide polymer is substantially accumulated within or about the cells of said culture, such accumulation perhaps causing and at least associated with aggregation of the cells of the culture, and thereafter recovering the accumulated polysaccharide polymer from said cells.

NATURE OF THE INVENTION

This invention relates to a useful polysaccharide polymer and to the process for its production. This polymer is synthesized by certain Gram-positive, rod shaped bacteria when they are cultured aerobically in a minimal salts medium containing a variety of carbohydrates and/or polysaccharides as carbon and energy sources. It is a glucan-type polysaccharide polymer that is synthesized and apparently is deposited externally as a capsule about the bacteria. In chemical composition, the polymer appears to resemble those B-1,3 glucans which can be isolated from certain strains of *Streptococcus faecalis* subsp. *myxogenes* and some species of Agrobacterium (Harada et al 1968) and are known as curdlans, but apparently is different in its gelation properties.

The polymer is produced by a bacterium that was isolated from decaying leaf litter. It was identified as *Cellulomonas flavigena* using standard bacteriological techniques, stated below, as described in the *Manual of Methods for General Bacteriology* (Smibert and Krieg, 1981).

The microorganisms which can be employed in this invention belong to the genus Cellulomonas, for example, *Cellulomonas flavigena* 819 which I isolated from leaf litter. The strain was deposited with the American Type Culture Collection (ATCC), Rockville, Md., USA and assigned the identification ATCC 53703. Also for example, *Cellulomonas flavigena* ATCC 482 and Cellulomonas sp. 13199 which were deposited with the ATCC and have been moved to permanent deposit status by me and my assignee parallel with and related to this patent application.

CHARACTERIZATION OF ISOLATES

A cellulolytic bacterium was isolated from soil using an enrichment medium containing cellulose as the only carbon source. Surface colonies of the isolate subcultured onto CM9-glucose agar were circular, convex, entire, smooth, opaque, yellow, and catalase positive. The KOH-test on these colonies indicated that the organism was Gram-positive. Gram stains of the cells produced mixtures of apparent Gram positive and Gram-negative bacteria. The results were interpreted as Gram-variability.

Growth in CM9-glucose semisolid motility medium was confined to the area of inoculation and was not inhibited by low oxygen levels near the bottom of the tube. The isolate appeared to be a non-motile facultative anaerobe. Examination of log phase CM9-glucose broth cultures by phase contrast microscopy confirmed that cells were not motile.

Cells from early-to-mid-log phase broth cultures were pleomorphic with swollen ends and pseudo-branching. Stationary phase cells appeared as short bacilli approximately 1.5 mm in length, and were encapsulated. Endospores were not detected in cells from either liquid or solid culture.

The biochemical characterization of the isolate is summarized in Table 1. The organism grew optimally at 30° C. and produced acid, but not gas, from all substrates utilized for growth. While the organism utilized pentoses, L-arabinose or D-xylose, it could not metabolize their enantiomers, D-arabinose or L-xylose. CM9-glucose medium not containing yeast extract did not support growth of the organism. Addition of either biotin or thiamine at a concentration of 1 mg/ml was sufficient to restore growth to control levels. CM9-glucose medium supplemented with both vitamins did not support growth any better than CM9-glucose medium containing only one of them. The organism required either biotin or thiamine, but not both. Based on these observations, the isolate was identified as *Cellulomonas flavigena* as described in the eighth edition of Bergey's *Manual Of Determinative Bacteriology* (Keddie, 1974). This strain is hereinafter referred to as "Cellulomonas Flavigena 819".

The polymer is produced by *Cellulomonas flavigena* 819 only when it is cultured in minimal salts media utilizing a variety of carbon and energy sources and, optimally, when a growth limiting amount of an inorganic nitrogen source is utilized. The minimal salts medium, designated as CM9, was of the following composition (g/L): KH2PO4, 9.091; K2HPO4, 5.817; MgSO4, 0.120; NH4Cl, 0.40; yeast extract (Difco), 0.500. Five milliliters of heavy metal solution (van Niel, 1971) was added to the minimal medium and the pH adjusted to 7.0. Thus, culturing of the organisms in complex, rich growth media, such as nutrient broth or brain-heart infusion broth, results in growth of the organism, but the cells do not aggregate and they do not produce polymer.

A variety of hexoses (e.g. glucose, fructose, galactose) or pentoses such as D-xylose or L-arabinose, or disaccharides such as sucrose or lactose, or a variety of corn starches and/or molasses, as well as non-carbohydrates such as glycerol, can be used as carbon and energy sources with the concomitant production of the polymer. Although *Cellulomonas flavigena* 819 is capable of growth on cellulose or hemicellulose, neither of these structural polymers are able to stimulate polymer production.

If growth media with the above listed, suitable carbohydrate substrates are not adequately buffered, then growth will be accompanied by a drop in pH, to about 4.5. This will result in growth inhibition prior to the synthesis of significant amounts of the polymer. Maximum polymer production is observed if the pH is not allowed to fall below 6. This can be accomplished by adequate buffering, incorporation of solid calcium carbonate into the medium, or use of alkali to control pH.

When optimal growth conditions are maintained, the bacteria begin to show aggregation during the initial 24 hours of incubation. Cultures are incubated at 30° C., with aeration (shaking at 250 rpm). Usually 72 hours incubation is sufficient to obtain maximum aggregation and maximum polymer production. At that time there are virtually no free cells, but, rather, virtually all of the bacteria have aggregated. Up to 75% of the dry weight of the aggregated cells can be accounted for as reducing sugar and most of that is representative of the polymer.

In addition to the new isolate of *Cellulomonas flavigena* 819, as described above, certain other bacteria which are members of the genus Cellulomonas are able to produce the polymer. These, together with their American Type Culture Collection numbers, are listed below, in order of decreasing efficiency of polymer production. With the exception of ATCC #21399, none were able to produce yields of polymer equivalent to that produced by the new isolate described above. The production by #21399 was nearly equivalent to that of the new isolate. The new isolate, although classified as *Cellulomonas flavigena*, differed from ATCC #482 (which is considered to be the type species) in that it did not require both thiamine and biotin for growth, and in its cellular morphology when grown under conditions that lead to aggregation of cells.

ATCC #21399 (Cellulomonas sp.)
ATCC #482 (*Cellulomonas flavigena*).
ATCC #491 (*Cellulomonas uda*)
ATCC #15724 (*Cellulomonas fimi*)
ATCC #2186 (*Cellulomonas cartae*)
ATCC #486 (*Cellulomonas biazotea*)
ATCC #482, in the equivalent media with respect to the subject polymer (CF 819), produces approximately 70% of the amount of polymer production of the C.f 819 polymer and that of ATCC #21399. Each of ATCC #491, #15724, #2186 and #486 produce but approximately 10% of the polymer produced by the subject organism (CF 819) and ATCC #21399 under the same growth conditions.

EXTRACTION AND PURIFICATION OF POLYMER

After incubation for 48–72 hours, agitation and/or aeration of the culture is terminated. The cells are allowed to settle. Most of the supernatant can then be removed by aspiration or decantation. The bacteria are then collected by centrifugation and the supernatant is discarded.

The polymer is conveniently extracted by resuspending the sedimented cells in 1 N NaOH, using 4 ml of alkali per gram (wet weight) of sedimented cells. After stirring for about 15 minutes, the suspension is again centrifuged to remove cell debris and the supernatant is collected by aspiration or decantation. While the supernatant is vigorously stirred, it is neutralized by the addition of either mineral acid (e.g. 6 N HCl ), or organic acid (e.g. 50% acetic acid). Upon neutralization of the alkaline supernatant, the polymer becomes insoluble, resulting in the congealing of the entire supernatant fraction. This gelled fraction can be further purified by suspending it in a large excess of water (e.g. 20 volumes) and, after stirring, allowing it to settle. After several cycles of resuspension in water, it is virtually pure.

The polymer can also be extracted with other strong bases, such as KOH. It cannot be extracted with 1 N ammonium hydroxide. It can also be extracted from bacterial cells which have dried by resuspending them in dimethylsulfoxide (DMS). After collecting the DMSO supernatants of such suspensions, the polymer may be precipitated from them by the addition of water. The polymer, however, is not purified as readily as when extracted with alkali. DMSO apparently extracts other cell substances which, under these conditions, coprecipitate with the polymer.

Extraction with cold NaOH (same proportions as used for room temperature extraction) appears to result in a modest increase in yield.

CHARACTERISTICS OF THE PRODUCT

Solubility Characteristics:

A. The product is soluble in 0.1 (or greater) NaOH and KOH.

B. The purified polymer is soluble in 85% (or more concentrated) formic acid.

C. The product is soluble in DMSO (Dimethylsulfoxide).

D. The product is poorly soluble in ammonium hydroxide.

E. With respect to the product, extraction with cold NaOH (same proportions as used for room temperature extraction) appears to slightly increase the yield of polymer.

F. The product is insoluble in water, methanol, ethanol, isopropanol and acetone.

Physical Characteristics

1. The polymer, in its gelled form, contains a very high proportion of water. When alkaline solutions of it are neutralized by the addition of either mineral or organic acids, or by dialysis, the polymer becomes insoluble and is precipitated as a gel. Washing the gel with water, followed by resuspension by means of rapid mechanical stirring, and then centrifugation of the suspension (e.g. at 15,000 x g for 15 min.) sediments the gel, of which 96–97% of the weight is accounted for by entrained water.

2. Aqueous suspensions of fully hydrated polymer are not further gelled by heating. (Kimura et al 3,822,250 Col. 6, 1. 70 et seq)

3. Heating of aqueous suspensions of the polymer does not result in solubilization of the polymer.

4. The hydrated form of the polymer, although up to 97% water in composition, is not free draining. Thus copious amounts of water are required to wash out small molecules which may be dissolved in the imbibed water.

5. Repeated cycles of dissolution in alkali followed by precipitation as a consequence of neutralization do not alter the physical properties of the polymer.

Chemical Characteristics

1. The polymer is reactive in the phenol sulfuric acid assay for reducing sugars. The analysis of a sample of highly purified polymer by this method reveals that the entire weight of the sample can be accounted for as glucose.

2. That the polymer is a glucan homopolymer, i.e. comprised of glucose subunits only, is further indicated by thin layer chromatograms of sulfuric acid hydrolyzates of it. These yield only one spot and it has a mobility relative to that of the front (Rf) which is identical to that of known glucose. Likewise, flame ionization gas liquid chromatography of trimethylsilyl derivatives of the hydrolyzate indicate that glucose is the only sugar component.

3. Its infrared spectrum exhibits significant absorption that bands at the wave numbers (cm-1): 3870, 3810, 3756, 3686, 3468, 3276, 2905, 1640, 1370, 1262, 1204, 1094, 889, 801, 661, 572, and 525.

4. C13 nuclear magnetic resonance spectral data were obtained by dissolving the polysaccharide in deuterated dimethyl sulfoxide. Chemical shifts were as follows: C-1: 103.448; C-2: 86.620: C-3: 76.630, C-4: 73.157; C-5: 68.723; and C-6: 61.190. (See Table I)

5. The infrared (IR) and nuclear magnetic resonance (NMR) spectra of the polymer indicate that it is a member of the curdlan family, i.e. it is a linear polymer comprised of B-1, 3-glucosidic linkages. The occurrence of 890 peak of absorption in IR spectrum is indicative of B-conformation. Its IR and NMR spectra are very similar to those of a polysaccharide polymer extracted from ATCC 21680 (listed as *Streptococcus faecalis* subsp. *myxogenes* in ATCC catalogue but renamed as Agrobacterium sp.). The polysaccharide polymer produced by *Streptococcus faecalis* subsp. *myxogenes* has been characterized as being a member of the curdlan family of B-1, 3-glucans (Harada et al., 1968).

6. Specific rotation (x)D 25 of polymer dissolved at a concentration of 10 mg polymer/ml of 0.1 N NaOH= +20.

Differences From Previously Described Curdlans

A. The gel formed by the neutralization of alkaline solutions of the polysaccharide polymer, followed by washing to remove extraneous substances, does not undergo change in gel structure as a consequence of heating. This is in contrast to the curdlans produced by *Streptococcus faecalis* subsp. *myxogenes* and certain of its mutants and certain strains of *Agrobacterium radiobacter* (Harada et al., 1968; Kimura et al., 1974, U.S. Pat. No. 3,822,25).

B. The specific rotations of curdlans described by Kimura et al., (U.S. Pat. No. 3,822,250) differ significantly from that of the polysaccharide polymer described here.

C. The infrared spectra of the curdlans described by Kimura et al. (U.S. Pat. No. 3,822,250) differ significantly from that of the polysaccharide polymer described here.

D. Colonies of the various species of Cellulomonas found to produce the polymer do not stain blue when grown on CM9-glucose media. This is in contrast to those of *Streptococcus faecalis* subsp. *myxogenes* and the *Agrobacterium radiobacter* which are known to secrete curdlan. Aniline blue is known to stain B-1, 3-glucans, Nakanishi et al (1974). Aniline blue, however, does stain PS 819 after it has been extracted from the indicated speciec of Cellulomonas. This may imply that in situ, prior to extraction, it is in a chemical complex with other cell components and is thereby protected from the stain.

Growth Media

The minimal medium, designated as CM9, was of the following composition (g/L): KH2PO4, 9.091; K2HPO4, 5.817; MgSO4, 0.120; NH4Cl, 0.40; yeast extract (Difco); 0.500. Five milliliters of heavy metal solution (van Niel, 1971) was added to the minimal medium and the pH adjusted to 7.0.

EXAMPLE 1

Synthesis of the polysaccharide polymer and encapsulation of the cell is dependent upon culture of the bacteria in a minimal salts media containing an organic carbon and energy source. The basal salts medium is comprised as follows (g/L): KH2PO4, 9.091; K2HPO4, 5.817; MgSO4, 0.120; yeast extract (Difco), 0.500. Five milliliters of heavy metal solution (van Niel, 1971) is added to the minimal medium and the pH adjusted to 7. Five hundred ml of the salts medium, containing 0.0075 M ammonium chloride as the nitrogen source, and 1% glucose as the energy source, is inoculated with 20 ml of a 24 hr. culture of *Cellulomonas flavigena* 819. The cultures are prepared in 2 liter baffled Erlenmeyer flasks. They are incubated at 30 C, with shaking at 250 rpm, for 3 days. Usually about 95% of the glucose added to the culture is utilized under these conditions. The aggregated, encapsulated cells are then collected by centrifugation of the culture fluid at 15,000 x g for 15 min. and the supernatant is discarded. The wet weight of bacteria produced and collected in this manner usually is about 45 mg/ml. The bacteria are then resuspended in 1.0 N NaOH and then stirred for 15 min. The alkaline cell suspension is then centrifuged for 15 min. at 15,000 x g. The precipitate is again extracted with 1 N NaOH, as above, and the supernatants, recovered by aspiration or decantation, while being stirred mechanically are neutralized with 50% acetic acid. The neutralization of the NaOH results in the gelation of the entire supernatant fraction. The gel is then resuspended in 10 liters of water in a precipitation jar. After brief stirring the hydrated polymer is allowed to settle. The clear supernatant is then removed by aspiration and the sediment again washed with water. After several such washing cycles the gel is collected by centrifugation at 15,000 x g for 15 min. About 3.8% of the weight of the precipitate collected in this way is from the polysaccharide and the remainder is accounted for by the imbibed water. The weight of the fully hydrated polymer produced in this way usually is 3.2 x the wet weight of aggregated cells collected from the culture. The hydrated polymer may be dried chemically, with acetone, or by lyophilization. The yield of dry polymer from 500 ml cultures produced in this way is about 5.5 gm, indicating a conversion of 55% of the glucose to polymer.

EXAMPLE 2

*Cellulomonas* sp. (ATCC #21399) is cultivated in the same manner as in Example 1. The yields of polymer produced, and the properties of the polymer, are virtually the same as those for the polymer produced by *Cellulomonas flavigena* 819.

EXAMPLE 3

*Cellulomonas flavigena* 819 may be cultured as in Example 1 excepting that other inorganic nitrogen sources may be used in place of NH4Cl. Thus KNO3, Na(NH4) HPO4, (NH4) 2HPO4, may all be used separately at concentration of 0.0075 M. The yields and properties of the polymer are similar to those of Example 2.

EXAMPLE 4

The polymer may also be produced by growth of *Cellulomonas flavigena* 819 in 1 liter Braun Biostat M fermentors, with the same medium used in Example 1. Such cultures are vigorously aerated and pH is controlled automatically. Yields equivalent to those in Example 1 are obtained if pH is maintained at 6.5–6.7. The advantage over flask cultures is that incubation period is reduced to 2 days.

EXAMPLE 5

The polymer may also be produced by the method of Example 1 except that carbon and energy sources other than glucose are used. Thus glycerol, D-xylose, fructose, galactose, sucrose, lactose, corn starch, and molasses, all at concentrations of 1%, may be used. The yields are approximately the same but there is variation in culture time. Thus, if glycerol is used it is necessary utually to incubate the culture for 4–5 days.

EXAMPLE 6

*Cellulomonas flavigena* (ATCC #482) is cultivated in the same manner as in Example 1. The properties of the polymer produced are the same as those for example 1. The yield, however, is about 70% of that produced as in Example 1.

TABLE I

| Characterization of Cellulolytic Isolate | |
|---|---|
| Cellular: | |
| Gram-positive; pleomorphic rods; nonmotile; asporogenous; encapulated. | |
| Metabolism: | |
| Biotin/Thiamine required | (+) |
| Inorganic nitrogen as sole N—source | (+) |
| Cellulolytic, amylolytic, xylanolytic | (+) |
| Utilization of: | |
| D-glucose, glycerol, L—arabinose, D-xylose, D-galactose, D-fructose, D-mannose, sucrose, lactose, acetate, maltose, D-trehalose, D-cellobiose, arbutin, salicin | (+) |
| Erythritol, adonitol, sulcitol, mannitol, meso-inositol, sorbitol, D-arabinose, azelate, D-ribose, L-xylose, L-sorbose, inulin, ethanol, propanol, butanol, pentanol, hexanol, heptanol, octanol, nonanol, adipate, malonate, | (−) |

TABLE I-continued

Characterization of Cellulolytic Isolate succinate, glutarate, pimelate, suberate,
propionate, butyrate, pentoate, p-hydroxybenzoate,
3,4-dihydroxybenzoate, 1,4-dutanediamine,
L—asparagine

TABLE II

1 R/30 S Peak Table

| Peak # | Peak | Peak Start | Peak End | % T |
|---|---|---|---|---|
| 1 | 3275.5 | 3285.2 | 3271.7 | 11.194 |
| 2 | 3468.4 | 3481.9 | 3464.6 | 15.258 |
| 3 | 1093.8 | 1140.1 | 1074.5 | 17.030 |
| 4 | 2905.2 | 2916.7 | 2895.5 | 34.293 |
| 5 | 1261.6 | 1286.7 | 1238.5 | 34.295 |
| 6 | 1369.6 | 1394.7 | 1334.9 | 49.967 |
| 7 | 1203.7 | 1223.0 | 1192.2 | 60.668 |
| 8 | 800.6 | 848.8 | 765.8 | 67.191 |
| 9 | 3869.7 | 3877.4 | 3867.8 | 76.735 |
| 10 | 3686.4 | 3690.3 | 3682.6 | 77.695 |
| 11 | 3755.9 | 3767.4 | 3746.2 | 87.243 |
| 12 | 3809.9 | 3813.7 | 3802.2 | 89.001 |
| 13 | 572.9 | 590.3 | 544.0 | 92.773 |
| 14 | 889.3 | 910.5 | 848.8 | 95.702 |
| 15 | 661.7 | 746.5 | 644.3 | 95.915 |
| 16 | 1639.7 | 1703.4 | 1601.1 | 101.040 |
| 17 | 524.7 | 530.5 | 522.8 | 102.410 |

THE PRIOR ART

Applicant is aware of the following patents directed to microbial polysaccharides.

Halleck No. 3,301,848, issued Jan. 31, 1967 "Polysaccharides And Methods For Production Thereof";

Kimura, et al No. 3,822,250, issued Jul. 2, 1974, for "Thermo-Gelable Polysaccharide".

Kimura et al No. 3,899,480, issued Aug. 12, 1975, for "Shaped Polysaccharide Particles And A Method For Producing Them";

Kang et al No. 3,915,800, issued Oct. 28, 1975, for "Polysaccharide And Bacterial Fermentation Process For Its Preparation".

Yokobayashi, et al No. 4,072,567, issued Feb. 7, 1978, for "Compound Water-Insoluble Glucan And Process For The Production Thereof".

Hisatsuka No. 4,146,706 issued Mar. 27, 1979, for "Polysaccharide And Process For The Production Thereof".

Williams, et al No. 4,298,725, issued Nov. 3, 1981, for "Process For The Preparation Of Polysaccharide 9";

Peik et al No. 4,529,797, issued Jul. 16, 1985 for "Hetero Polysaccharide S-198".

Sutherland No. 4,638,059, issued Jan. 20, 1987 for "Gel-Forming Polysaccharides".

Literature references include the following:

Harada, T., M. Masada, K. Fujimori, and I. Maeda. 1966. Agr. Biol. Chem., 30: 196-198.

Harada T., A. Misaki, and H. Saito. 1968. Arch. Biochem. Biophys. 124: 292-298.

Keddie, R. M. 1974. In R. E. Buchanan and N. E. Gibbons (eds.). Bergey's Manual Of Determinative Bacteriology, 8th ed. p. 629-631. Williams and Wilkins Co., Baltimore, MD.

Kimura, H., et al. 1974. U.S. Pat. No. 3,822,250.

Nakanishi, I., K. Kimura, T., M. Ishikawa, I. Banno, T. Sakane, and T. Harada. 1974. J. Gen. Appl. Microbiol., 22: 1-11.

Sandford, P. A. and J. Baird. 1983. Industrial Utilization Of Polysaccharides. In The Polysaccharides, Vol. 2, pp. 411-490. G. O. Aspinall (ed.). Academic Press, Inc.

Smibert, R. M. and N. R. Krieg, 1981. In P. Gerhardt, R. G. E. Murray, R. C. Costilow, E. W. Nester, W. A. Wood, N. R. Krieg, and G. B. Phillips (eds.) Manual of Methods for General Bacteriology. p. 409-443. Am. Soc. for Microbiol. Washington, D.C.

van Niel, C. B. 1971. In A. S. Pietro (ed.)., Methods in Enzymology vol. XXIII, part A., p. 3-28. Academic Press.

Abstract: Role of Capsules In The Aggregation of *Cellulomonas flavigena* K. C. Voepel and C. S. Buller, University of Kansas, Lawrence, Kans. (Presented At Missouri Valley Branch, American Sociology For Microbiology, Kansas City, MO. Apr. 1986.)

GENERAL DESCRIPTION

I have discovered a bacterial cell that produces a polymer under certain conditions of growth. These conditions comprise furnishing a minimal medium in which a carbon and energy source, such as glycerol, glucose, galactose, xylose, arabinose, lactose, sucrose, starch, or molasses is provided in excess. Under such conditions the bacterial cell produces a water insoluble polymer comprised solely of glucose subunits. The polymer remains cell bound during throughout the preparation of the cell culture.

After the so above energized cells are separated from the culture media by centrifuging, the polymer produced by the cell (and bound therein or thereon) can be solubilized and extracted in such as sodium hydroxide or dimethylsulfoxide (DMSO), thus going into liquid solution.

Thereafter, the solubilized, extracted polymer may be precipitated as a gel by neutralizing the alkali in the sodium hydroxide or potassium hydroxide, or by removing the alkali by dialysis. It may be precipitated from the DMSO extracts by the addition of water thereto.

This precipitate can be purified to yield a polysaccharide polymer composed only of glucose. The polymer is not cellulose, glycogen or starch.

Other glucose homo-polysaccharide polymers include pachyman, laminarinan, curdlan, cellulose and starch. As previously noted, it is definitely known that the polymer is not cellulose, starch or glycogen.

Under the conditions noted above, the bacterium produces a polysaccharide polymer. This polymer is a glucan, i.e. it is composed only of glucose subunits. It is water insoluble. The polymer is tightly bound to the bacterial cell.

The precipitate purifies as a polysaccharide polymer, composed only of glucose subunits. The glucose subunits are covalently linked by B-1, 3-glucosidic bonds.

While certain other bacteria may produce glucans, it should be noted that few are known to produce glucans that are both water insoluble and are able to form gels when alkaline solutions thereof are neutralized. Thus, while many bacteria can produce small amounts of glycogen (a glucan), such is not typically completely insoluble in water. A few bacteria are able to produce curdlan, a glucan which is water insoluble. Curdlan, however, may differ in that it has been stated that aqueous suspensions of it become clear when heated to about 54° C. and they apparently form thermally irreversible gels when heated to higher temperatures.

FURTHER CHARACTERIZATION

This is a bacterial polymer which can reversibly form gels. The particular polymer can readily be obtained from a certain newly isolated strain of cellulotic bacteria. This polymer is produced when the bacteria are grown in a culture medium in which the nitrogen source is available only in growth limiting amounts. The polymer can be extracted into 1 N NaOH. When such extracts are neutralized with either mineral or organic acids, the polymer forms a water insoluble gel.

The polymer is produced by a new strain of *Cellulomonas flavigena* here designated 819. The polymer producing strain was selected from chemostat cultures in which ammonium chloride was the growth limiting metabolite.

When the polymer is produced, it apparently is stored as a capsule which may surround the bacterium. The polymer itself has been determined to be a polysaccharide. Under optimal growth conditions as much as 65% to 75% of the dry weight of the encapsulated bacteria can be accounted for as reducing sugar.

The polymer is completely soluble in 1 N NaOH. When this solution is neutralized with either mineral or organic acids, a water insoluble gel is formed. If the gel is macerated and diluted in water, then subjected to a centrifugal force of 16,000 times g for 15 minutes, 96% of the weight of the precipitated gel is accounted for as water.

With respect to the harvesting of cultures and extraction of polymer, a desirable characteristic of the encapsulated bacteria is that they sediment rapidly, thereby facilitating their recovery. After removing the clear upper layer of the culture by decantation or aspiration, the sedimented bacteria can be collected by centrifugation. After washing the precipitated cells with water, they will be resuspended in 1 N NaOH and the suspension will be stirred mechanically at room temperature for 30 minutes. The insoluble cell residues can be removed by centrifugation.

The combined supernatants will be adjusted to pH 5.5 or lower with hydrochloric acid. After maceration of the gel which forms, it will be washed with water to remove salts and soluble cell debris.

With respect to the growth substrates, it has been established that the polymer is produced when the bacteria are grown in media in which the carbon and energy source is one of a variety of hexoses, pentoses, or glycerol or polysaccharide polymers such as starch. Preliminary experiments have indicated that the polymeric capsule is also produced when relatively inexpensive substrates such as molasses are used.

The bacteria used in these studies were originally isolated on the basis of their ability to hydrolyze cellulose and hemicellulose and then utilize the liberated monosaccharides as a carbon and energy source. In wild type bacteria, capsule production during growth on these inexpensive and renewable substrates is prevented by catabolite repression. Mutants which have lost the capability of catabolite repression, however, can readily be isolated. The potential for generating the polymer from inexpensive, renewable cellulosic and hemicellulosic substrates greatly enhances the economic feasibility of the process.

With respect to stability, long term stability of the gel has been studied over a period of at least 6 months. The term syneresis is used in the literature to describe the expulsion of solvent (water in this case) from the gel. None has been detected yet. The anhydrous polymer is stable at refrigerator and room temperatures. The gel is not altered by heating.

BRIEF PROCESS DESCRIPTION

The following steps describe the culture of the organism, the separation of the aggregated cells from the supernatant, dissolution of the polymer capsule in either sodium hydroxide, KOH or DMSO with discard of the precipitate of the extracted cells, treatment of the supernatant including the dissolved or solubilized polymer, and then recovery from the (sodium hydroxide) supernatant by neutralizing (adding acid) or adding particular solvents such as ethanol or propanol. Also, recovery from DMSO by addition of water.

(1) Select any species of Cellulomonas (preferably the subject bacterium, which is here named as *Cellulomonas flavigena* 819 or another: ATCC #21399 (Cellulomonas sp.) or ATCC #482 (*Cellulomonas flavigena*)).

(2) Cultivate such organism in minimal media, which may be defined as almost any carbohydrate carbon source, particularly such as glucose, starch, sucrose, ribose, xylose, etc., plus a source of inorganic nitrogen such as ammonium chloride. This culture is incubated, with aeration, for approximately three days.

(Minimal media is defined as such where, with the exception of the carbon source, all of the constituents are inorganic and the concentrations of all of the media components are known; as opposed to, for example, a nutrient broth).

(3) The culture is allowed to settle or is centrifuged or both settled and centrifuged. Ultimately, the settled cells, including the polymer capsules, are collected by centrifugation.

(4) The sedimented cells are extracted with sodium hydroxide solution (0.5 N to 2.5 N have been used effectively.) Potassium hydroxide (KOH) can be employed. Ammonium hydroxide (NH4OH) is not a strong enough base.

(The polymer dissolves in concentrated formic acid, as does curdlan, and can be precipitated therefrom by the addition of water. Use of formic acid also would be more expensive.)

(4) (a) Alternatively, dry cells may be extracted with dimethylsulfoxide (DMSO). This polymer preparation, however, contains more impurities that do preparations prepared with NaOH.

(5) With respect to the sodium hydroxide extraction, after centrifugation of the extracted cells, the separated supernatant carrying the dissolved polymer is neutralized with acetic acid or hydrochloric acid. The viscosity of the gel that forms as a result is dependent upon the concentration of the polymer as it is dissolved in the alkali. Gels which have been resuspended and washed in water, then sedimented by centrifugation at 16,000 x g are about 96% water.

(5) (a) In the DMSO extraction, such having been centrifuged to produce a clear supernatant, the separated supernatant is diluted with water, thus giving a DMSO supernatant and a precipitate which contains, among other things, the polymer.

(6) After the gel has formed it is resuspended in a volume of water which is at least 10 times that of the gel. The viscous suspension for several minutes. After stirring has been terminated the hydrated polymer is allowed to settle out and the overlaying water may be siphoned off. This water washing procedure is repeated for several cycles to purify the polymer, each time decanting or siphoning off the water.

(7) The partly water separated product is centrifuged at 16,000 g for 20 minutes. The precipitate is the polymer gel, including 96% water.

(8) The latter can be freeze dried (lyophilized) or dried with organic solvents, including methanol, ethanol and acetone. In the latter, a ten fold volume of the solvent is added and the mixture centrifuged, to sediment the polymer. It may then be dried by evaporation of the solvents.

(9) The powdered polymer thereafter can be dissolved in sodium hydroxide or potassium hydroxide. The pure polymer will dissolve in 0.1 N NaOH. Additionally, the polymer may be dissolved in formic acid (85% or greater strength), whereupon adding water will precipitate the gel. Also after the NaOH gel is dried, the pure polymer dissolves in DMSO.

UTILITY AND COMMERCIAL USAGE

With respect to the known utility of polysaccharides in general (and microbial polysaccharides specifically), reference is made to Sandford, P. A., and J. Baird. 1983. Industrial Utilization Of Polysaccharides. In the Polysaccharides, Vol. 2, p. 411–490, G. O. Aspinall (ed.). Academic Press, Inc.

With respect to the microbial polysaccharides, in said Chapter 7, written by Messrs. Paul A. Sanford and John Baird, it is noted that, as with higher living organisms, a common feature of bacteria and fungi is the ability to produce exocellular polysaccharides. It is further stated that only in recent times, the past three decades or so, has the practicality of production on a large scale and commercial marketing of microbial polysaccharides been seriously worked with. A table (XXXIII *Microbial Polysaccharides*) not only lists then currently in production microbial polysaccharides, but also such saccharides which were then regarded as significant candidates for commercial production. One of the latter is curdlan, sourced as *Agrobacterium faecalis* and *Alcaligenes faecalis*.

Only two commercially available microbial polysaccharides, specifically, Xanthan gum (*Xanthomonas campestris*) and dextran ((NRRL 512 F) strain of *Leuconostoc mesenteroides*, for example) are listed. Dextran refers to a large class of exocellular bacteria polysaccharides composed of a-D-glucopyranosyl residues.

Other microbial polysaccharides listed include Scleroglucan which is a term given to a class of neutral exocellular polysaccharides secreted by certain fungi (for example genus Sclerotium sp.) This is also Polytran (Pillsbury) and Actigum CS (French company CECA). Also noted are curdlan, pullulan, Beijerinckia Indica polysaccharides (PS-7) (Merck), Zanflo-10 polysaccharide (PS-10) (Merck), *Pseudomonas elodea* polysaccharide (PS-60) (Merck), bakers yeast glycan and bacterial alginate.

Also see *Extracellular Microbial Polysaccharides-A Critical Overview*, 1977, Sandford & Larkin (Eds.) Am. Chem. Soc., ACS Symposium Series 45.

SUMMARY

The subject process thus produces a B-1, 3-glucan type of polysaccharide polymer PS-819 in which the producer organism is cultivated in a certain type of growth medium which facilitates the synthesis and accumulation of an excess of the polymer, as well as the procedure for the extraction and purification of the polymer. *Cellulomonas flavigena*, strain 819, isolated and characterized as described above, is the organism of preference. Second thereto, as organism of preference, is Cellulomonas sp. ATCC 21399. Third choice of the organism is *Cellulomonas flavigena* ATCC 482. The other Cellulomonas known available species *uda* ATCC 491, *fimi* ATCC 15724, *cartae* ATCC 21681 and *biazatea* ATCC 486 are the organisms of least choice with respect to the group of seven organisms.

The product of the process is a polysaccharide polymer, PS 819, containing only glucose subunits which are covalently linked via B-1, 3-glucosidic bonds having the characteristics above delineated.

From the foregoing, it will be seen that this invention is one well adapted to attain all of the ends and objects hereinabove set forth together with other advantages which are obvious and which are inherent to the process.

It will be understood that certain features and subcombinations are of utility and may be employed without reference to other features and subcombinations. This is contemplated by and is within the scope of the claims.

As many possible embodiments may be made of the invention without departing from the scope thereof, it is to be understood that all matter herein set forth is to be interpreted as illustrative and not in a limiting sense.

I claim:

1. A process for the preparation of polysaccharide polymer, comprising the steps of:
   providing a quantity of bacteria selected from the group consisting of Cellulomonas sp. (ATCC No. 21399), *Cellulomonas flavigena* (ATCC No. 482) and *Cellulomonas flavigena* 819 (ATCC No. 53703);
   culturing said bacteria in a nutrient medium including an excess of assimilable carbon and energy sources, the pH of said medium being maintained at a level of above about 6 during said culturing step,
   said culturing step being carried out until the occurence of cell aggregation and concomitant formation of cell-bound $\beta$ 1,3-glucan polysaccharide polymer; and recovering said polysaccharide polymer.

2. The process of claim 1, said pH being maintained at a level of from about 6 to 7.

3. The process of claim 1, said culturing step being carried out for a period of from about 48 to 96 hours.

4. The process of claim 1, said medium including an excess of carbon and energy sources taken from the group consisting of glycerol, glucose, galactose, xylose, arabinose, lactose, sucrose, starch, molasses, fructose and mixtures thereof.

5. The process of claim 1, said medium further including a source of inorganic nitrogen.

6. The process of claim 1, said recovery step comprising the steps of separating said cells from the culture medium by centrifugation, solublizing said polymer and extracting the same in a strong alkali solution or DMSO.

* * * * *